(12) United States Patent
Tartakovsky et al.

(10) Patent No.: US 7,474,400 B2
(45) Date of Patent: Jan. 6, 2009

(54) MULTI-WAVELENGTH FLUOROMETRIC SYSTEM AND PROBE FOR MONITORING OF BIOPROCESSES

(75) Inventors: Boris Tartakovsky, Cote-St-Luc (CA); Serge Guiot, Montreal (CA)

(73) Assignee: National Research Council of Canada, Ottawa, Ontario (CA)

( * ) Notice: Subject to any disclaimer, the term of this patent is extended or adjusted under 35 U.S.C. 154(b) by 101 days.

(21) Appl. No.: 11/602,309

(22) Filed: Nov. 21, 2006

(65) Prior Publication Data

US 2007/0064228 A1 Mar. 22, 2007

Related U.S. Application Data

(63) Continuation-in-part of application No. PCT/CA05/01153, filed on Jul. 21, 2005.

(60) Provisional application No. 60/591,085, filed on Jul. 27, 2004.

(51) Int. Cl.
G01N 21/64 (2006.01)
(52) U.S. Cl. .................. 356/317; 356/318; 250/461.1
(58) Field of Classification Search ............. 356/317, 356/318, 417
See application file for complete search history.

(56) References Cited

U.S. PATENT DOCUMENTS 5,491,343 A 2/1996 Brooker 6,537,829 B1 3/2003 Zarling et al.
6,646,770 B2 11/2003 Lee et al.
2003/0058440 A1* 3/2003 Scott et al. .................. 356/318

FOREIGN PATENT DOCUMENTS

WO WO-03/002959 1/2003

OTHER PUBLICATIONS

Russell et al., Multiple Excitation Fluorometer For In Situ Ocenographic Applications, *Applied Optics*, vol. 36, No. 6, Feb. 20, 1997.

* cited by examiner

*Primary Examiner*—F. L Evans
(74) *Attorney, Agent, or Firm*—Hans Koenig

(57) ABSTRACT

A fluorometric system for on-line monitoring of biological processes uses a plurality of light sources, each with a different spectral width, to illuminate a sample, the light sources selected to produce emission of fluorescent light, and usually also dispersed light, from the illuminated sample. One of the light sources has a wide spectral range. The light sources are operated sequentially or in combination. Spectra acquired from the emitted light are combined and processed to evaluate properties of the sample, such as concentration of the fluorescing components or particle concentration. The system preferably uses an electro-optical probe in which excitation optical energy is transmitted to the sample directly from the light sources, typically LEDs, without an optical waveguide.

17 Claims, 8 Drawing Sheets

MULTI-WAVELENGTH FLUOROMETRIC SYSTEM AND PROBE FOR MONITORING OF BIOPROCESSES

CROSS-REFERENCE TO RELATED DOCUMENTS

This application claims the benefit of U.S. application Ser. No. 60/591,085, filed 27 Jul. 2004, and is a continuation-in-part of PCT application no. PCT/CA2005/001153 filed 21 Jul. 2005.

FIELD OF THE INVENTION

This invention relates to systems for measuring properties of certain samples, and more particularly, to fluorometric systems for on-line monitoring of biological processes.

BACKGROUND OF THE INVENTION

External perturbations as well as population variability often result in broad fluctuations of growth and production rates of microorganisms. Close monitoring of a bioprocess is required to maximize process efficiency. Because of a lack of reliable on-line monitoring techniques, most often on-line bioprocess monitoring is limited to biogas analysis for oxygen and carbon dioxide content, while such key process parameters as substrate and product concentrations are only measurable off-line. Consequently, the results are available with a significant delay from the time of sampling. This delay leads to untimely process diagnosis as well as limits process control to pre-programmed feed strategies.

Recently developed on-line monitoring methods use flow injection analysis (FIA) techniques as well as near- and mid-infrared spectrometry (Tosi et al, Biotechnol. Prog., 19, 1816-1821 (2003)). While these techniques have been used successfully at the laboratory scale, high equipment cost is prohibitive for most industrial applications.

The use of fluorometry for rapid detection of fermentation imbalances and metabolic activities has already been demonstrated. Most often, fluorescence is measured by illuminating the sample at one wavelength and measuring fluorescence at another (higher) wavelength, i.e. a single excitation—single emission technique is used. In particular, NADPH-dependent fluorometry has been used for monitoring fermentation as well as aerobic and anaerobic wastewater treatment processes. However, bioreactor broth contains large amounts of proteins, amino acids, and other fluorescent compounds that interfere with NADPH-related fluorescence thus limiting industrial applications of single excitation—single emission fluorometry. The quality of monitoring can be improved by using multiple-excitation multiple-emission fluorescence measurements (e.g. Tartakovsky, B.; Lishman, L. A.; Legge, R. L., Water Research, 30 (12), 2941-2948 (1996)). In this technique, both excitation and emission wavelengths are varied to obtain two-dimensional spectra For this reason, this technique of fluorometric measurement, also employed herein, is often called two-dimensional fluorometry. The spectra are often processed using multivariate statistical analysis methods, such as Partial Least Square (PLS) regression, which provides a linear relationship between analytical measurements and multi-wavelength spectra.

To select a desired excitation wavelength, the light should pass through a monochromator or a filter wheel. The fluorescence signal (emission spectrum) can be measured by using a second monochromator or a filter wheel followed by a spectrometer. Alternatively, a close caption detector (CCD) array spectrometer can be used. Notably, the use of a monochromator or a filter wheel increases the setup cost and dimensions as well as it increases the scan time.

Light emitting diodes (LEDs) produce high intensity light in a narrow range (20-30 nm) of wavelengths. Thus, LEDs can be used for sample illumination at a fraction of the cost of conventional light sources equipped with monochromators or filter wheels. Indeed, some LED light sources are commercially available (LS-450, Ocean Optics Inc., Dunedin, Fla., USA). While LEDs are often used for illumination in the visible range of wavelengths, the use of LEDs for UV applications is relatively new. The UV LEDs are constantly improving with some newer LEDs emitting light at 350 nm (RLT350-30, ROITHNER, LASERTECHNIK, Vienna, Austria).

Fluorometers or similar devices have been described in patent literature as well. Some of the devices use LEDs. U.S. Pat. No. 6,825,927 (Goldman et al.) and U.S. Pat. No. 6,873,417 (Bahatt et al.) are examples of the prior art in this respect.

It is also known to use various optical waveguide arrangements to transfer light from the light source to the sample to be illuminated and to transfer the light (also fluorescence light) emitted by the sample to the measuring instruments. Exemplary patents are U.S. Pat. Nos. 6,791,687 and 6,166,804.

While the use of LEDs has reduced the cost of the fluorometric apparatus, there is still a room for improvement of the accuracy and reliability of the on-line monitoring of bioprocesses, e.g. food processing or wastewater treatment.

SUMMARY OF THE INVENTION

The invention attempts to meet the above improvement objectives. In particular, simultaneous fluorescence of several components, which limits application of fluorescence-based measurements in bioreactor monitoring, can be dealt with by acquiring fluorescence spectra at various excitation wavelengths and at different combination of excitation wavelengths. This increases total amount of information on fluorescence and reflection properties of the sample and improves accuracy of simultaneous measurements of culture broth components such as microorganisms, substrates, intermediates, and products.

In accordance with one aspect of the invention, there is provided a fluorometric system comprising
- an excitation light source for illuminating a sample to generate emission light therein, the excitation light comprising at least two diverse light sources with different spectral width,
- means for activating the diverse light sources sequentially,
- a detector for detecting the emission light and producing spectral input from the emission light, and
- a processor for evaluating properties of the sample based on the combined spectral input.

In an embodiment of the invention, the system uses a novel probe which is normally placed such that one end of the probe is disposed adjacent to or proximate to the sample. In contrast to standard optical probes, the probe of the invention comprises the excitation light source disposed at the end of the probe adjacent to the sample. For the purpose of fluorometric measurements as described herein, the probe comprises a broadband light source and a monochromatic light source, both sources disposed proximate to the sample for transmitting unguided light energy to the sample.

In one embodiment of the invention, the excitation light source is a set of light emitting diodes. Energy emitted from the sample in response to the excitation energy is transmitted to a detector, typically a spectrometer, via an optical fiber that is partly disposed in the probe to transmit light emitted from the sample to the light detector In accordance with another aspect of the present invention, there is provided a fluorometric system suitable for monitoring biological processes, the system comprising:

an excitation light source disposed to illuminate a sample to generate emission of light from the sample, the excitation light source comprising a filter-free broadband light source preferably including a UV/VIS wavelength range, and at least one monochromatic light source, a light detector for detecting the at least fluorescent light emitted from the sample and for acquiring spectra of the emitted light from the broadband light source and from the at least one monochromatic light source, a processor coupled to the detector for evaluating the sample based on analysis of the spectra acquired by the light detector, and control means for activating sequentially or simultaneously the broadband light source and the monochromatic light source or one of the monochromatic light sources, wherein the processor comprises means for combining and analyzing a plurality of spectra produced by the light detector by detecting spectral input produced sequentially or simultaneously by the broadband light source, the monochromatic light source or sources and a combination of the monochromatic light sources.

The excitation light is in part scattered (reflected) by solid particles within a culture broth (cells, solids, etc). This reflected light is measured by the spectrometer. Another part of the excitation light is absorbed by the fluorescent particle and the light is emitted at a higher wavelength, also measured by the spectrometer. Because of the use of a "broadband" (UV/VIS) excitation light, at each wavelength the signal measured by the spectrometer consists of two components: reflection (same wavelength as excitation light) and fluorescence (coming from the excitation at a lower wavelength). In the absence of solid particles, the reflection signal (scattered light) measured by a fiber-optic reflection probe with coaxial excitation and emission fibers (i.e. at an excitation-emission angle of 180°) will be negligible.

In some embodiments, the filter-free broadband light source has a wavelength range from about 200 nm to about 800 nm, and the excitation light source encompasses a plurality of monochromatic light sources, at least some of them being in the UV range. The monochromatic light sources can be LEDs. The "broadband" may denote a combination of light from several LEDs and then the range may be non-continuous i.e. may consist of several ranges, each defined by a single LED.

In accordance with yet another aspect of the invention, there is provided a method for fluorometric analysis of biological processes, the method comprising providing an excitation light source comprising a broadband (multiwavelength) light source and at least one monochromatic light source, for illuminating a sample, activating sequentially the broadband light source and the at least one monochromatic light source to cause sequential emission of light, detecting the sequential emission of light to generate sequential spectral input, and analyzing the sequential spectral input to produce combined spectra representative of fluorescence compounds present in the sample.

In an embodiment of the invention, the step of sequential activation may include activation of a combination of monochromatic lights.

BRIEF DESCRIPTION OF THE DRAWINGS

The invention will be explained in more detail by way of the following description in conjunction with the drawings, in which FIG. 6b is a graph representing VSS measurements in the same location as in FIG. 6a, and FIG. 6c is a graph representing COD measurements in the same location as in FIG. 6a.

DETAILED DESCRIPTION OF THE INVENTION

Figure 1:
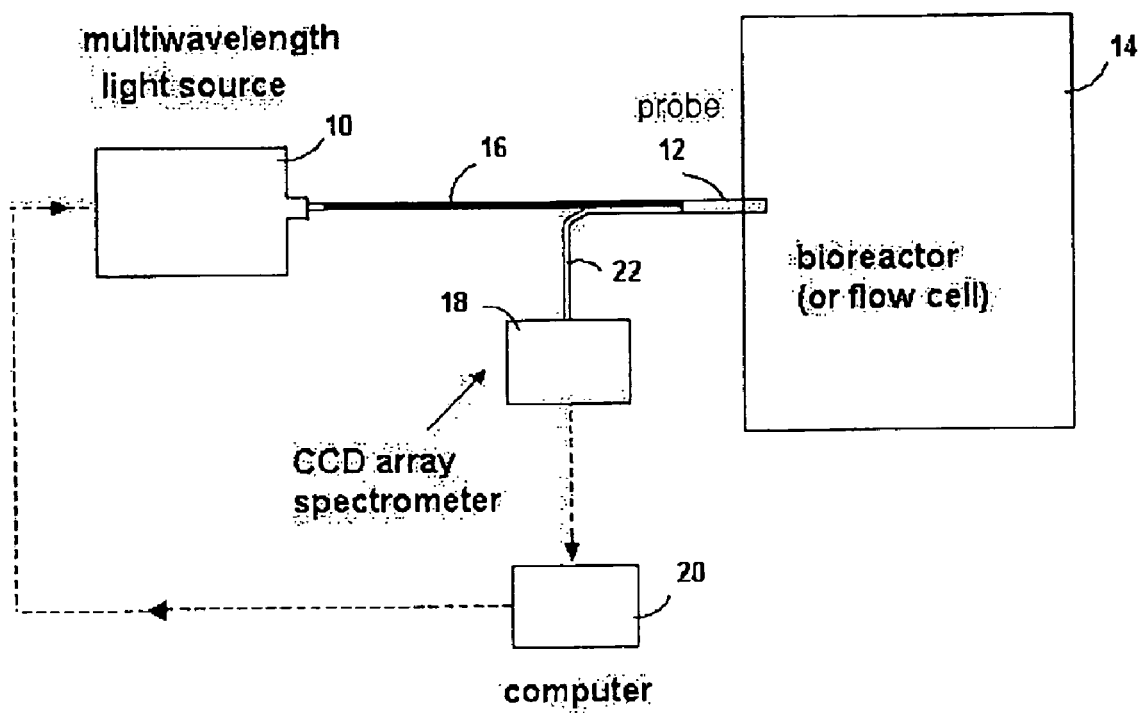
FIG. 1 represents schematically an embodiment of the fluorometric system of the invention.

In general terms, the fluorometric system for on-line bioprocess monitoring, as represented in FIG. 1, employs a multiple light source 10, an optical probe 12 shown as mounted on a bioreactor 14 and coupled optically to the light source 10 via an optical waveguide 16, a CCD (close caption detector) spectrometer 18 (JSB 2000 from Ocean Optics Inc., FL, USA) for acquiring fluorescence and other emission light data, and a computer-based data processing unit 20 operatively connected to the spectrometer 18 and to the light source 10. The probe 12 is coupled to the spectrometer 18 through another optical waveguide 22.

Figures 2A, 2B, 2C:
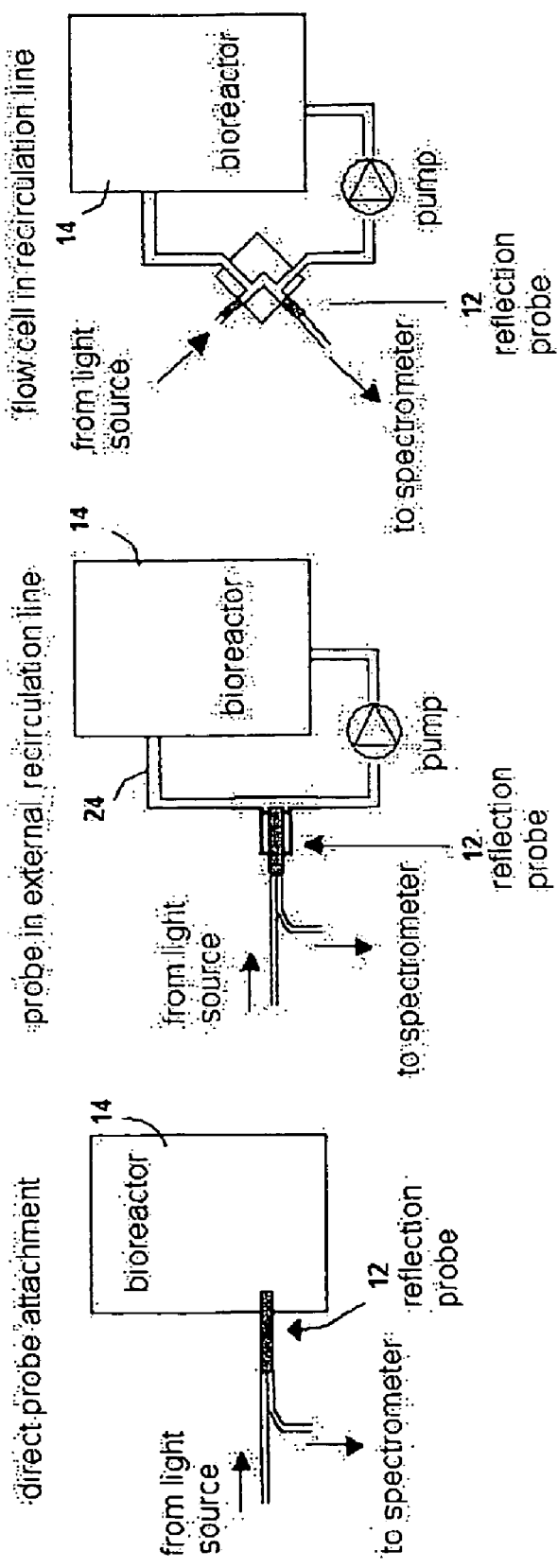
FIGS. 2a, 2b and 2c represent various configurations of probe attachment in the system.

The probe 12 may be mounted directly on the bioreactor 14 as shown in detail in FIG. 2a. Alternatively, it may be mounted on an external recirculation line 24 of the bioreactor 14 (FIG. 2b) or in a flow cell 26 installed on the recirculation line 24 (FIG. 2c). If a flow cell is used, fluorescence is measured using two windows positioned at an angle to each other (e.g. 45° or 90°).

Figure 3A:
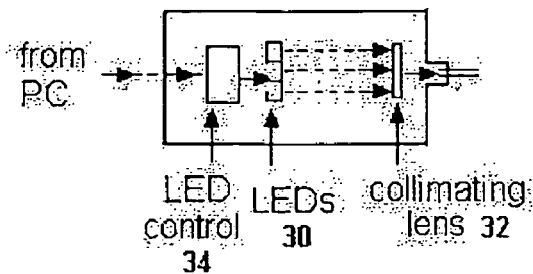
FIG. 3a illustrates a LED assembly of the excitation light source.
Figure 3B:
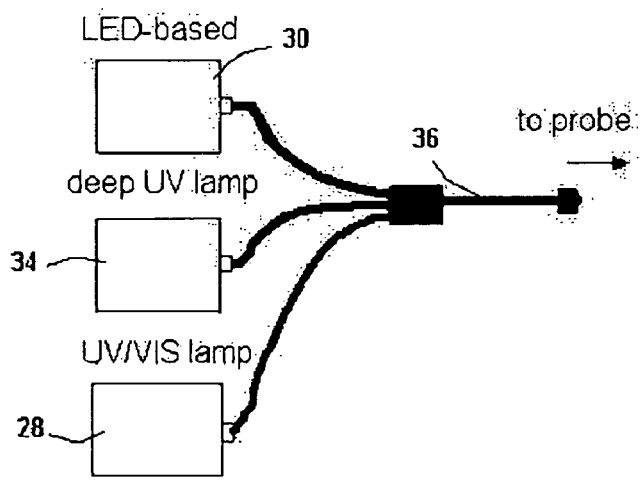
FIG. 3b illustrates an exemplary arrangement of the components of the excitation light source.
Figure 3C:
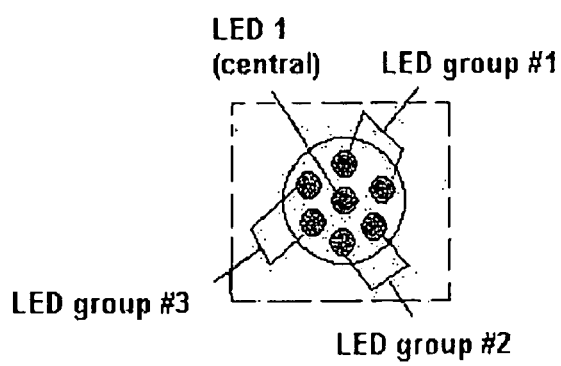
FIG. 3c is a front view of an exemplary LED assembly of FIG. 3a, FIG. 3d is a longitudinal sectional view of an embodiment of a probe for fluorescence measurements.

The multiple (multiwavelength) light source 10 combines several light sources in a single unit (FIGS. 3a-3c). It includes a broadband light source 28 that emits light in an ultra-violet and visible (UV/VIS) range of wavelengths, e.g. a pulsed xenon lamp (200-750 nm). It also includes several light emitting diodes (LEDs) 30, each of which emits light in a narrow range of wavelengths, approximately 30 nm. For instance, a set of LEDs with peak wavelengths at 375, 400, 420, and 450 nm can be used. A schematic representation of the LED-based part of the multiwavelength (MW) light source 10 is shown in FIGS. 3a and 3c. In this setup, the LEDs are attached in a circular arrangement around a central LED. The light output of each LED is transferred to the light source output by means of a collimating lens, e.g. 25 mm collimating lens 32. The output of the light source is connected to an optical fiber 16 (FIG. 1) using a connector, e.g. SMA-type connector. The LEDs are controlled either manually by switches placed on the light source cover or automatically by computer using external TTL-level signal unit 34. The LEDs can be grouped, e.g. in groups of two identical LEDs, 2, 3 and 4 around a central LED 1, as shown in FIG. 3*c*, to increase light intensity. Alternatively, up to 3 LEDs can be connected using a bifurcated or a trifurcated fiber with a sufficiently large diameter (e.g. 600 µm) to reduce light losses.

Modern UV LEDs emit light starting from 350 nm (e.g. RLT350-30 by ROITHNER, LASERTECHNIK, Vienna, Austria). While the technology is constantly improving, a lower wavelength UV light is desired for detecting proteins and other components with a maximum of fluorescence at the excitation wavelengths below 350 nm. This can be achieved by adding another xenon or a deuterium lamp 34 equipped with a low-pass optical filter (below 350 nm) to the light source setup 10. The outputs of all lamps can be combined by a trifurcated fiber 36 (e.g. an optical fiber with a three-way coupler) as shown in FIG. 3*b*.

Instead of a pulsed xenon lamp, a broadband light source for the purpose of the invention can be realized by combining several LEDs with excitation peaks in the UV and VIS range of wavelengths. The outputs of the various light sources can be combined using a n-furcated (e.g. bifurcated or trifurcated) fiber or a collimating lens thus providing a multi-wavelength light source instead of a single UV/VIS broadband lamp. Thus, the term "broadband light source" should be understood quite liberally as this term encompasses both a UV/VIS light source producing a continuous broadband signal and a combination of several LEDs producing light in a non-continuous wavelength range.

The multiple light source 10 and the spectrometer 18 of the fluorometric system are controlled by a computer in order to acquire fluorescence spectra at different excitation wavelengths. The lights are turned on sequentially and corresponding spectra are acquired by the spectrometer and stored in the computer memory. As explained previously, a simultaneous irradiation by several LEDs can be used to obtain a combined fluorescence/scattering spectrum, similar to that obtained using a UV/VIS lamp. This technique can be used either to reduce the number of lamps in the MW light source or to obtain an additional spectra at a different profile of excitation wavelengths.

In operation, a computer-based algorithm controls the light source 10 to activate sequentially, in intervals ranging from several milliseconds to several seconds, the broadband light source (which, as explained above, may itself be a combination of light from several light sources) and one or more of the remaining "monochromatic" light sources (LEDs, deuterium lamp with filter etc.). The light beams thus sequentially produced are passed to the probe 12 to illuminate a biological sample in the reactor 14 as shown for example in FIG. 2*a*. If the sample contains fluorescent compounds, e.g. proteins, light emission produced by the sample and passed to the CCD spectrometer 18 will provide a fluorescence spectrum. If the light beam is a broadband light, the spectrum produced by the sample may contain both fluorescence and scattered light.

The spectra sequentially detected by means of the spectrometer 18 are then analyzed by the computer 20. To this end, spectra derived from various components (broadband or monochromatic) of the light source 10 are combined by the algorithm to carry out the analysis. The computer synchronizes the multiple light source 10 and the CCD array spectrometer 18 via the control unit 34. The computer 20 also carries out data storage and processing functions. A more detailed description of the algorithm follows.

In the arrangement illustrated in FIG. 1, the probe 12 is a conventional optical probe (reflection probe) providing excitation energy to the sample and receiving emission from the sample. Typically, the conventional probe consists of two fibers joined in an enclosed stainless steel ferule on one end and split at the other end (bifurcated fiber). One of the fibers 16 is connected to the light source 10 and is used to deliver excitation light to the sample (illumination fiber). The second fiber 22 (read fiber) is used to transmit the fluorescence to a spectrometer 18. The diameter of the probe is 5 mm or less. One drawback of such reflection probe is a significant light loss in the illumination fiber at the light source-air-glass interface. Depending on the fiber diameter and other parameters, 80-95% of the light source signal can be lost. While this performance is acceptable for many applications, in other cases higher illumination intensity may be required. In particular, novel UV LEDs can emit light at a wavelength of 250 nm, however the light intensity is almost an order of magnitude lower than in LEDs with an excitation wavelength of 350 nm and above. Consequently, the application of 250 nm LEDs in the reflection probe setup is limited to highly fluorescent media. In addition, the intensity of the fluorescence signal is directly proportional to the intensity of the light source and therefore measurement time and the interval between the measurements can be reduced if light losses are reduced.

Figure 3D:
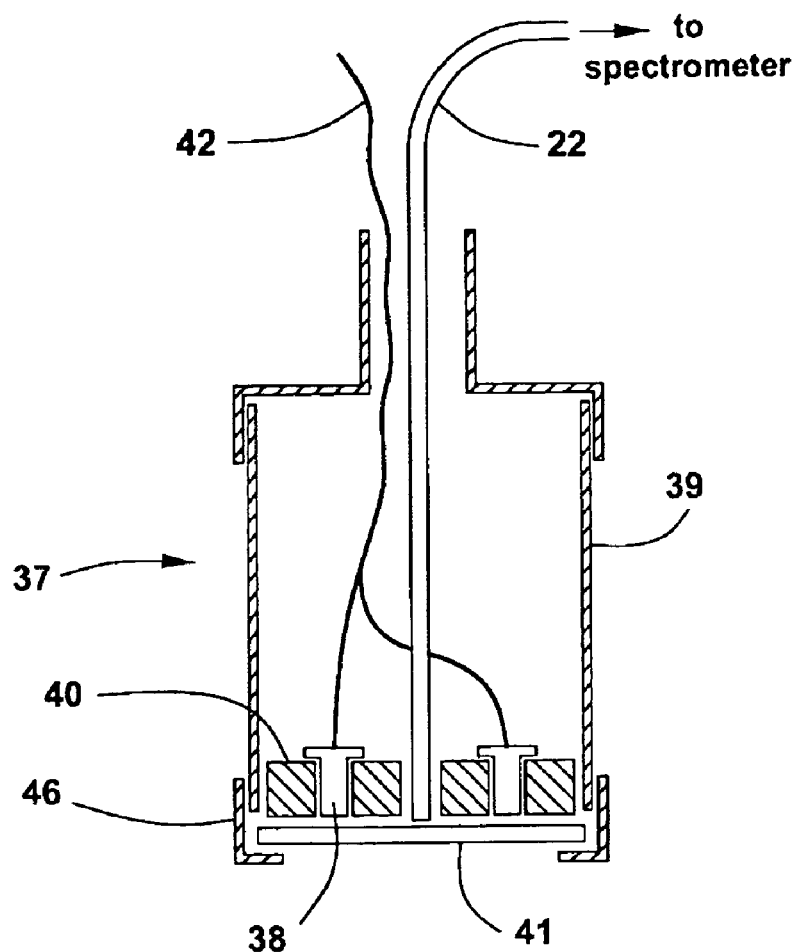
FIG. 3e is a cross-sectional view of the probe of FIG. 3d.

In accordance with another aspect of the invention, it is proposed to use a novel electro-optical probe which incorporates the functionality of both the light source 10 and probe 12 of FIG. 1. As shown in FIG. 3*d*, the probe 37 has a number of LEDs 38 mounted in a holder at the tip of the probe, therefore the illumination fiber 16 is not required for sample illumination. The fluorescence signal of the sample is transmitted to a spectrometer by an optical (read) fiber 22, as in the arrangement of FIG. 1.

Figure 3E:
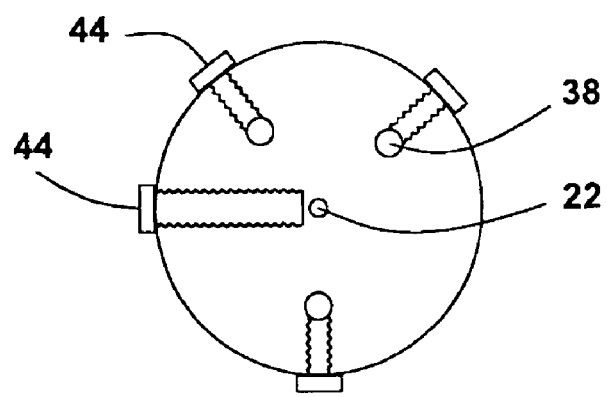

As shown in FIGS. 3*d* and 3*e*, the probe 37 of the invention has a housing 39 which is terminated with a quartz window 41. The LEDs 38 (only three shown for clarity) are assembled substantially concentrically around the optical fiber 22 (read fiber) using a holder 40 and are controlled via electrical wiring 42. The LEDs 38 and the read fiber 22 are attached to the holder 40 using bolts 44. A threaded cover 46 is used to attach the holder and the quartz window to the probe. The maximal number of LEDs depends on the diameter of the probe, the typical LED diameter being 5 mm.

As mentioned above, the probe 37 of FIGS. 3*d*-3*e* functions both as a light source 10 and a probe 12 of FIG. 1. The read fiber 22 provides emission signals from the sample to the spectrometer 18. The functionality of diodes 38 is the same as that of the light source 10 of FIG. 1.

It will be appreciated that one of the differences between a standard optical probe (e.g. R400-7, Ocean Optics Inc., Dunedin, Fla., USA) and the electro-optical probe of FIGS. 3*d* and 3*e* is that the optical energy transmitted to the sample from the source (LEDs or equivalents) is unguided and the waveguide (illumination fiber 16) between the source and the sample is eliminated.

For the purpose of illustration, assuming that the multiple light source of the invention includes a UV/VIS light source and five LEDs (FIG. 3*b*), an exemplary spectrum acquisition run is as follows:

| 1. | UV/VIS | read spectrum #1 |
| 2. | LED 1 | read spectrum #2 |
| 3. | LED 2 | read spectrum #3 |
| ... | ... | ... |
| 6. | LED 5 | read spectrum #6 |
| 7. | LEDs 1-5 | read spectrum #7 |

At the end of the run, spectra #1-#7 are processed together i.e. combined by the algorithm and analyzed to generate data representative of sample properties.

Figure 4:
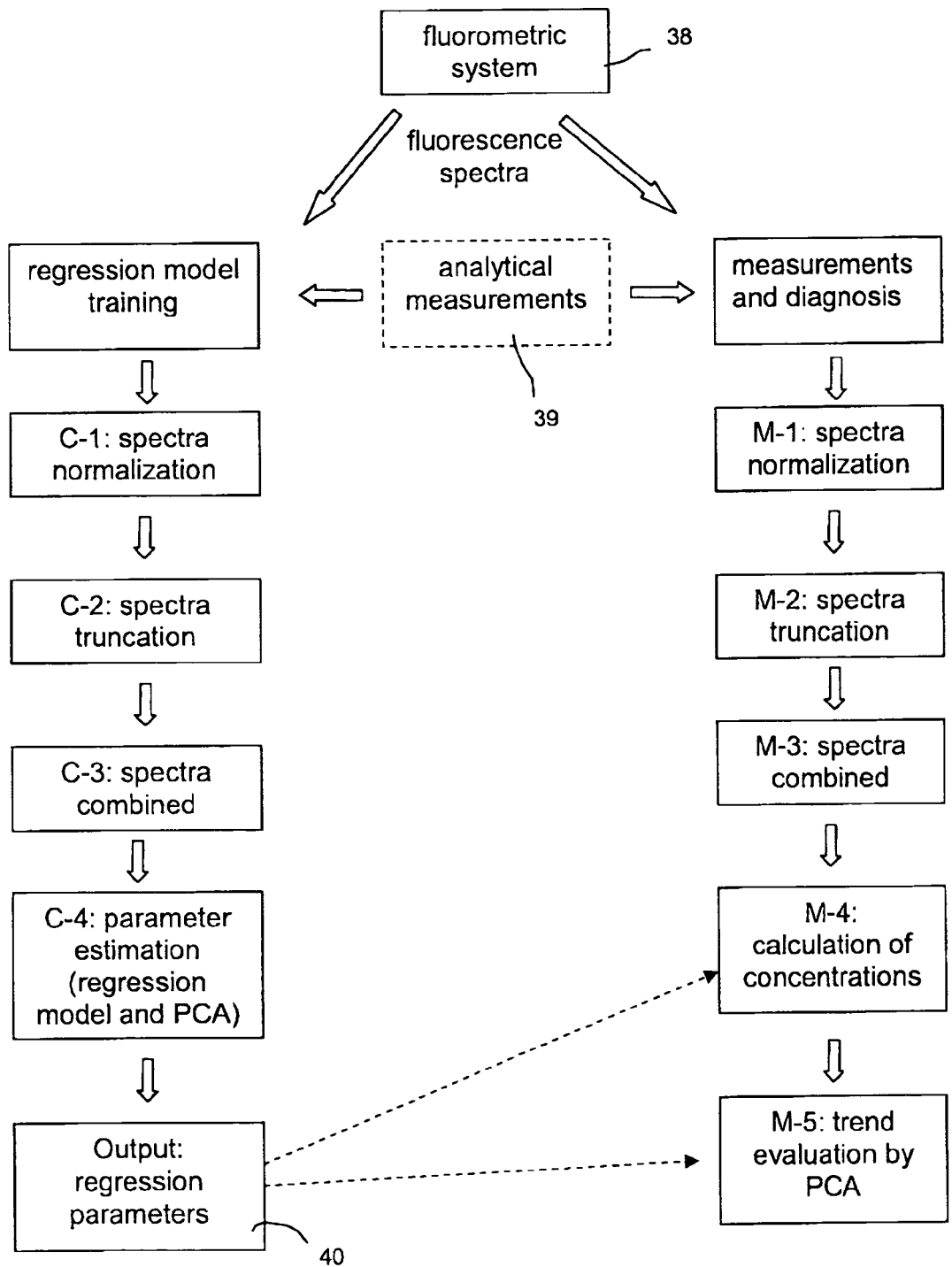
FIG. 4 is a schematic diagram of spectrum acquisition and processing.

At a given instant in time, the sample is characterized by several fluorescence spectra, each obtained at a different excitation wavelength or wavelength range. These two-dimensional fluorescence spectra are processed using multivariate statistical methods, such as partial least squares (PLS) and principal component analysis (PCA) algorithms. While PLS regression is used to evaluate concentrations of target components, principal component analysis is used to estimate process trends for diagnostic purposes. In addition, spectral areas can be used to correlate fluorescence signals with such process parameters as chemical oxygen demand (COD), and biological oxygen demand (BOD). Notably, COD and BOD concentrations reflect total content of complex organic materials in the liquid. An overall functional diagram of spectral analysis, including the software-executed steps, is shown in FIG. 4 in which the fluorometric system (generally designated as 48) generates fluorescence spectra for use in regression model training (left column, steps C1-C4) and measurements and diagnosis (right column, steps M1-M5). Analytical measurements (box 49) are carried out periodically in parallel with the fluorometric measurements for comparison. The output of the calibration steps (box 50) is provided to steps M4 and M5 of the measurement sequence. The software carries out the functions of data collection, data storage, regression model calibration, and measurements.

The software function of model calibration infers analytical measurements with fluorescence spectra acquired at the time of sampling. The calibration procedure requires several (e.g. ten or more) measurements for successful calibration. The following sequence of calculations is used for model calibration:

Step C-1. Fluorescence spectra acquired using at least UV/VIS (broadband) and monochromatic light sources are normalized by computing each spectrum area and dividing each element of the corresponding spectrum by the area (e.g. the spectra are normalized to 1).

Step C-2. Fluorescence spectra are truncated so that only areas containing significant fluorescence and/or reflection signals are retained.

Step C-3. The spectra acquired at each data acquisition interval are combined in a linear array representing one acquisition cycle.

Step C-4. A calibration procedure is carried out by inferring the spectra with available analytical measurements using a regression model (e.g. PLS regression model). Simultaneously, the normalized and combined spectra are used to calculate the principal components (PCs) for principal component analysis (PCA). The output of the calibration procedure is a set of regression model parameters, which can be used to carry out the measurements and process diagnostics.

The following sequence of calculations is used for MW fluorescence-based measurements:

Step M-1: At each data acquisition step, the normalization procedure is carried out in agreement with step C-1 (see above) by computing each spectrum area and dividing each element of the corresponding spectrum by the value of the area.

Step M-2: Fluorescence spectra are truncated as described in step C-2.

Step M-3: The spectra are combined in a linear array representing one acquisition cycle.

Step M-4: Concentrations of process components are computed using model parameters estimated in the calibration procedure (step C-4).

Step M-5: Process trends are estimated using principal components (PCs) computed in step C-4.

Notably, steps C-3 and C-4 are compulsory for obtaining regression models, while steps C-1 and C-2 can be omitted. Accordingly, steps M-1 and M-2 should be omitted if steps C-1 and C-2 are not carried out during the calibration procedure.

It will be understood that each light source provides partial characterization of the sample. A combination of several spectra obtained at different excitation wavelengths allows for more accurate measurements. It can be noted that the spectra acquired using an UV/VIS (200-700 nm) light source contain both fluorescence and scattered light. Because light scattering depends on the amount and size distribution of solid particles, the spectra obtained with the UV/VIS light source can be inferred with such parameters as cell density and/or total (soluble and solid materials) chemical oxygen demand (COD). Usually, bioreactor broths as well as wastewaters contain large amounts of fluorescent materials. Consequently, sequential spectra acquisition using several light sources is required for accurate measurements of various components, as illustrated in the example below.

EXAMPLE

Measurements of total CODs, volatile fatty acids (VFAs), and volatile suspended solids (VSS) were carried out in a 5 L anaerobic reactor. The fluorometric setup was equipped with a multi-wavelength light source containing Xenon (200-700 nm) and UV LED (380 nm) connected by a bifurcated fiber with a reflection probe installed in the external recirculation line of the reactor.

The fluorometric measurements according to the invention were carried out for a period of 25 days. Chemical oxygen demand and volatile suspended solids (VSS) were measured periodically according to Standard Methods (APHA, AWWA and WEF. (1995) *Standard Methods for examination of water and wastewater*. American Public Health Association. Washington). VFA concentrations were measured using a gas chromatograph. Fluorescence spectra were acquired in 10 min intervals with background acquisition prior to each fluorescence measurement.

The measurements were performed with a fluorometric system which consisted of a Xenon (PX-2, Ocean Optics Inc., Dunedin, Fla., USA) and a 380 nm LED light sources connected by a bifurcated fiber to an R400-7 fiber optic reflection probe with 6 illumination fibers and one read fiber, and an USB2000 CCD array fiber optic spectrometer (Ocean Optics Inc., Dunedin, Fla., USA). The spectrometer used a UV/VIS grating with a spectral range of 250 to 800 nm and a resolution of 0.9 nm. The fiber optic probe was inserted into the external recirculation loop of the reactor. Fluorescence was measured from the front surface.

Figure 6A:
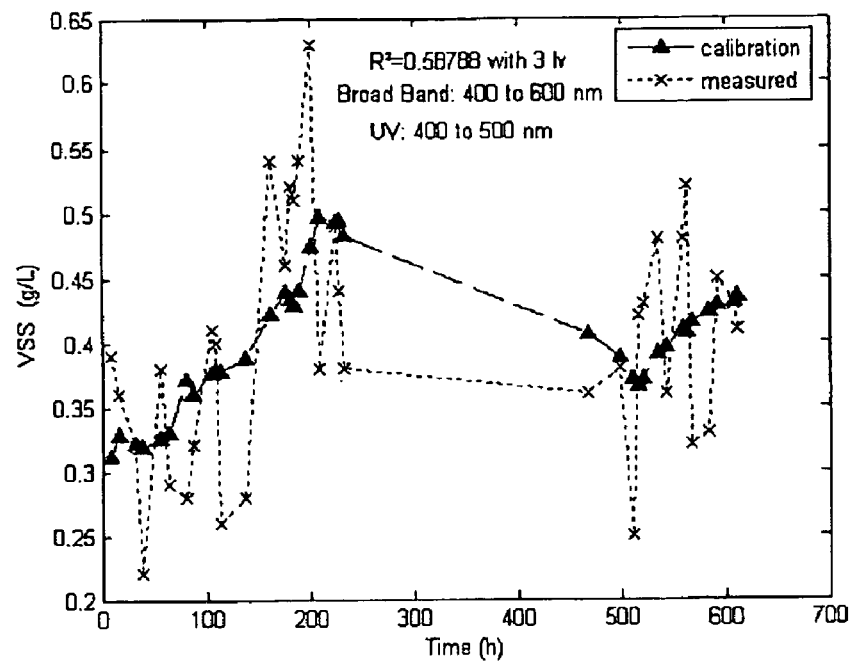
FIG. 6a is a graph representing results of calibration of a Partial Least Squares (PLS) model of VSS measurements in the recirculation loop of an anaerobic reactor.
Figure 6B:
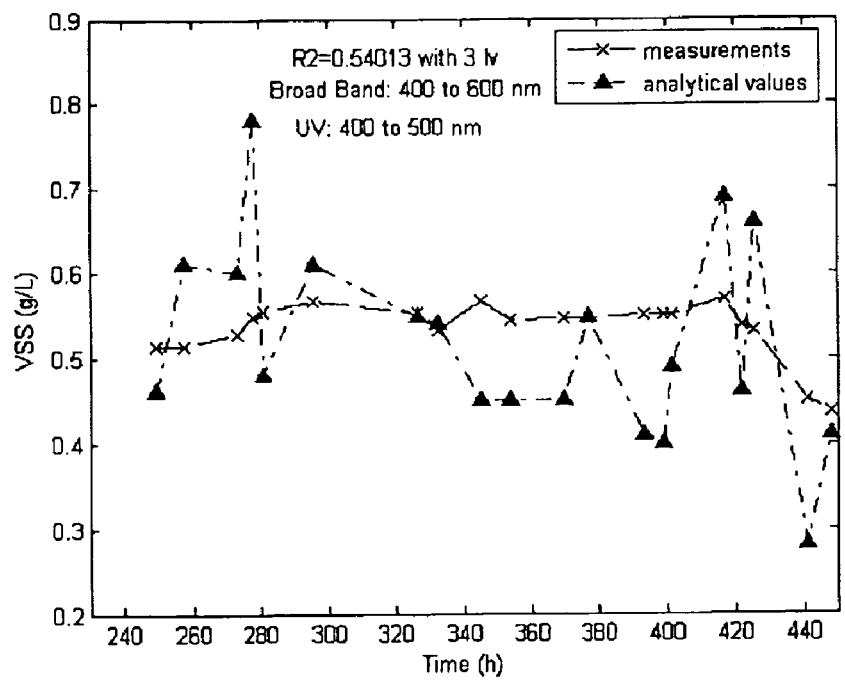
Figure 6C:
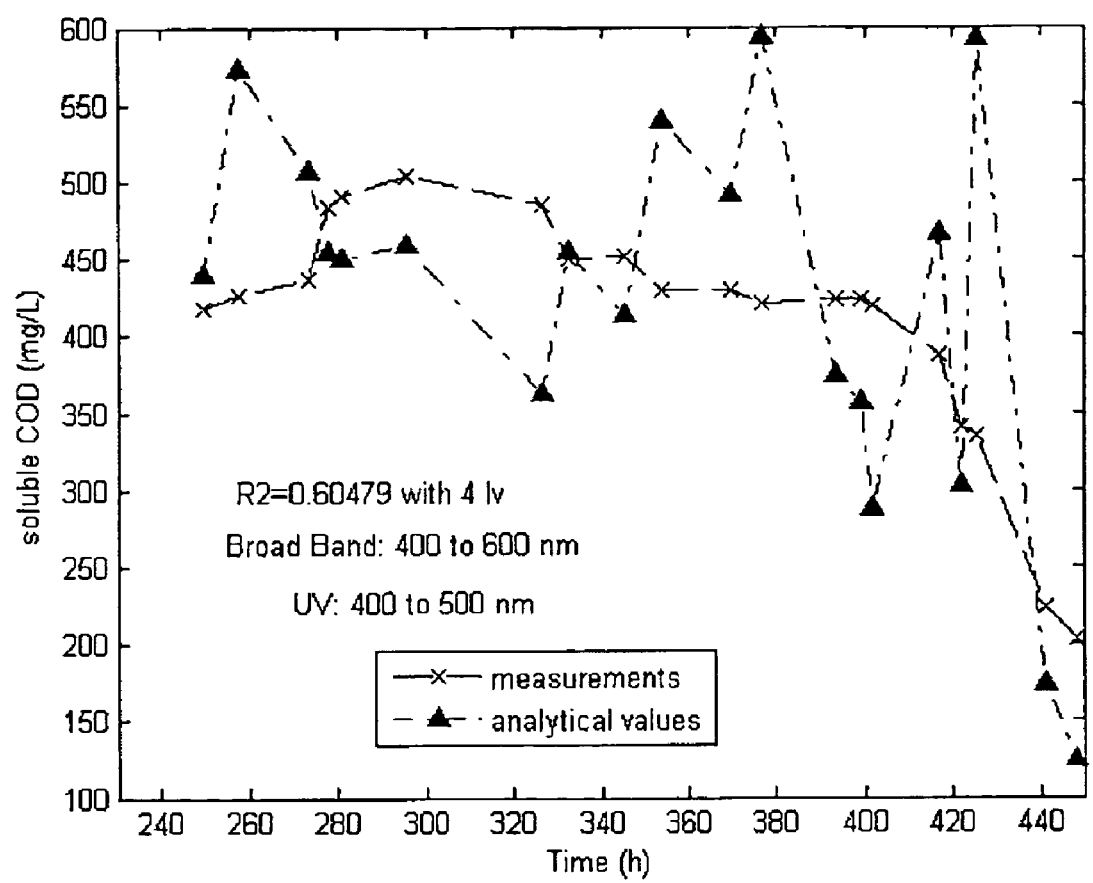

Two fluorescence spectra corresponding to excitation with UV/VIS (200-700 nm) and LED UV (380 nm) were obtained at each acquisition period. The data were divided into "calibration" and "validation" (18 days) sets. The calibration data set was used to estimate parameters of PLS regression models describing the dependence of COD and VFA concentrations on fluorescence spectra. The validation data set was used to compare fluorescence-based and analytical measurements. The quality of fluorescence-based measurements was estimated using correlation coefficient ($r^2$). A comparison of calibration and validation accuracies using either both spectra (UV/VIS and UV at 380 nm), or UV/VIS alone, or UV 380 nm is given in Table 1. This comparison shows that a combination UV/VIS and UV 380 nm light sources provided better accuracy for both calibration and validation measurements. Also, the advantage of using two light sources was more pronounced for total COD and VSS measurements (higher $r^2$ values for validation with two light sources, see Table 1) because these parameters include particulate organic materials. It can be noted, that analytical measurements of VSS strongly depend on the sampling procedure. Sample inhomogeneity often results in large variations of the measurements as can be seen in FIGS. 6a and 6b. Consequently, fluorescence-based measurements significantly improved the accuracy both for training (FIG. 6a) and validation (FIGS. 6b and 6c) data sets.

TABLE 1

Comparison of correlation coefficients obtained with different combinations of light sources. Xenon lamp was used to obtain UV/VIS light in 200-700 nm and LED UV had a peak at 380 nm. To reduce noise, the emission spectra were truncated to 400-600 nm for UV/VIS excitation and to 400-500 nm for UV 380 nm excitation. Calculations were carried out using PLS regression models with 4 latent variables (CODs and VFAs) and 3 latent variables (VSS).

| light source | total COD | | VFAs | | VSS | |
| --- | --- | --- | --- | --- | --- | --- |
| | calibration | validation | calibration | validation | calibration | validation |
| UV/VIS & UV | 0.78 | 0.60 | 0.80 | 0.57 | 0.60 | 0.54 |
| UV/VIS | 0.73 | 0.23 | 0.65 | 0.29 | 0.60 | 0.42 |
| UV | 0.74 | 0.58 | 0.80 | 0.53 | 0.60 | 0.40 |

Overall, the use of multi-wavelength light source, which provided sequential sample illumination in a broad range of wavelengths (UV/VIS, 200-700 nm) and in a narrow UV range of wavelengths (370-390 nm) provided superior accuracy of COD and VSS measurements in comparison with a single light source.

Figure 5:
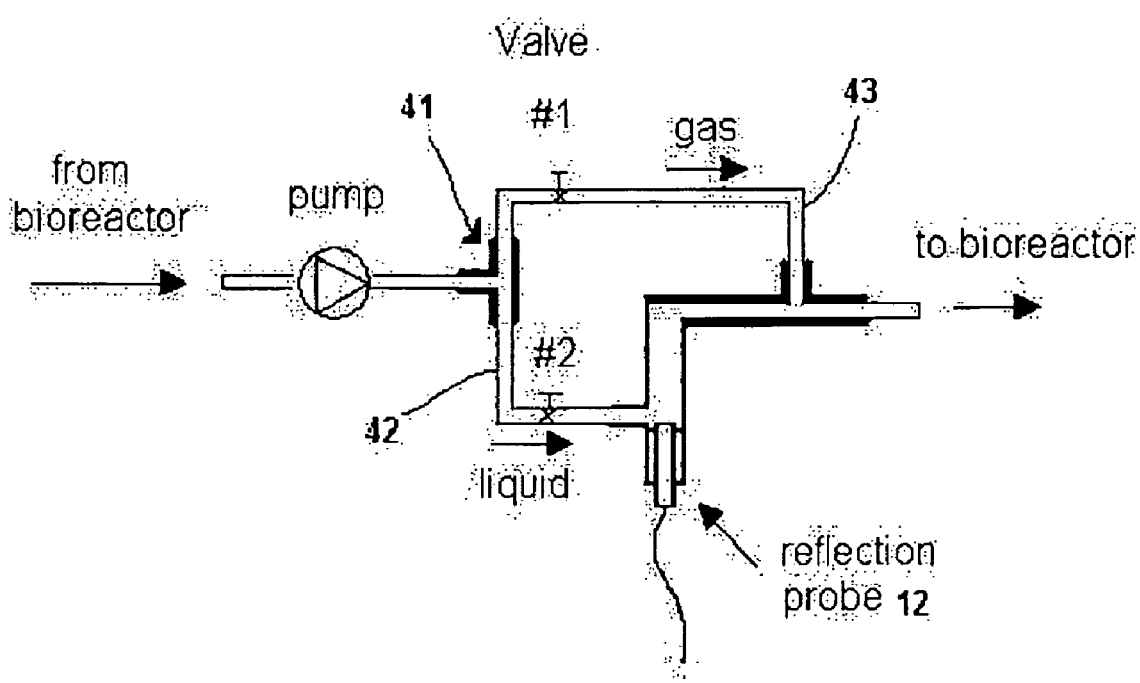
FIG. 5 illustrates liquid-gas separation for fluorescence measurements.

According to another aspect of the invention, the amount of gas bubbles in the external recirculation loop can be reduced by addition of a bypass line (FIG. 5). Notably, the presence of gas bubbles in the liquid sample considerably affects fluorescence measurements. The bypass line essentially begins before the fluorescence probe. At the bifurcation point 51, gas and liquid are separated by gravity. The probe 12 is installed at the lower branch 52 of the bifurcated line, which contains a minimal amount of gas bubbles. The upper branch 53 contains gas and excess liquid. The two streams then merge after the probe. Flow distribution between the two lines is controlled by means of valves #1 and #2.

Numerous modifications and alternative embodiments of the invention will be apparent to those skilled in the art in view of the foregoing description. For example, LEDs can be replaced with laser diodes or other equivalents. Accordingly, this description is to be construed as illustrative only and is only for the purpose of teaching the best mode of carrying out the invention. It is intended that the present invention be limited only to the extent required by the appended claims and the applicable law.

The invention claimed is:

1. A fluorometric system suitable for monitoring biological processes, the system comprising:
   an excitation light source disposed to illuminate a sample to generate emission of light from the sample, the emitted light including fluorescent light, the excitation light source disposed at one end of a probe, the probe having the one end disposed adjacent to or proximate to the sample, wherein the excitation light source comprises a filter-free broadband light source and at least one monochromatic light source,
   a light detector for detecting the light emitted from the sample,
   a processor coupled to the detector for evaluating the sample based on spectral analysis of the emitted light,
   control means connected operatively with the processor and the excitation light source for activating sequentially or simultaneously the broadband light source and the monochromatic light source or one of the monochromatic light sources, wherein the processor comprises means for evaluating properties of the sample based on combined spectral input produced sequentially or simultaneously by the broadband light source, the monochromatic light source or sources and a combination of the monochromatic light sources.

2. The system according to claim 1, wherein the broadband light source is a UV/VIS light source.

3. The system according to claim 1, wherein the broadband light source is a plurality of monochromatic light sources.

4. The system according to claim 1, wherein the at least one monochromatic light source is a light emitting diode or diodes.

5. The system according to claim 4, wherein at least one of the light emitting diodes emits light in an ultraviolet range.

6. The system according to claim 1, wherein the broadband light source emits light of spectral width from about 200 to about 800 nm.

7. The system according to claim 1 wherein the probe comprises said broadband light source and said monochromatic light source, both sources disposed proximate to the sample for transmitting unguided light energy to the sample.

8. The system according to claim 1 wherein the excitation light source is a set of light emitting diodes.

9. The system according to claim 1 wherein the probe further comprises an optical fiber disposed to transmit light emitted from the sample to the light detector.

10. A fluorometric system comprising
   an excitation light source for illuminating a sample to generate emission light therein, the excitation light source comprising at least two diverse light sources with different spectral width,
   means for reducing the amount of gas bubbles in the sample prior to the illumination thereof,
   means for activating the diverse light sources sequentially,
   a detector for detecting the emission light and producing spectral input from the emission light, and
   a processor for evaluating properties of the sample based on the combined spectral input.

11. The system according to claim 10 wherein the means for reducing is a bypass line connected to a sample container, the bypass line defining a gravity gas-liquid separator, the excitation light source being coupled with the bypass line downstream from the separator.

12. A method for fluorometric analysis of biological processes, the method comprising
   providing an excitation light source comprising a broadband light source and at least one monochromatic light source, for illuminating a sample,
   activating sequentially the broadband light source and the at least one monochromatic light source to cause sequential emission of light from the sample,
   detecting the sequential emission of light to generate sequential spectral input, and
   combining and analyzing the sequential spectral input to evaluate properties of the sample, the combining and analyzing comprising normalizing spectra by computing each spectrum area and dividing each spectrum element by the area.

13. The method according to claim 12 wherein the excitation light source comprises a plurality of monochromatic light sources and the step of sequential activation includes simultaneous activation of the plurality of monochromatic lights.

14. The method of claim 12 wherein the step of combining and analyzing includes estimating trends of the biological process.

15. A probe for fluorescence measurements of biological samples, the probe comprising
   an enclosure having an end to be disposed proximate to a sample,
   a plurality of light sources disposed at the end of the enclosure for unguided transmission of light to the sample, and
   an optical waveguide having a first end disposed at the end of the enclosure and a second end for transmitting optical signals from the sample to an optical detector.

16. The probe according to claim 15 wherein the plurality of light sources is arranged substantially concentrically relative to the first end of the optical waveguide.

17. The probe according to claim 15 wherein the plurality of light sources are light emitting diodes.

* * * * *